United States Patent [19]

Fischer et al.

[11] Patent Number: 4,751,322

[45] Date of Patent: Jun. 14, 1988

[54] MONOMER PURIFICATION

[75] Inventors: Stephen A. Fischer, South Amboy; Dinshaw F. Bardoliwalla, Randolph; Reuben H. Grinstein, Denville; Gary L. Speenburgh, Parsippany, all of N.J.

[73] Assignee: Diamon Shamrock Chemical Co., Dallas, Tex.

[21] Appl. No.: 855,965

[22] Filed: Apr. 25, 1986

[51] Int. Cl.$^4$ ............................................. C07C 67/48
[52] U.S. Cl. ...................................................... 560/218
[58] Field of Search ......................................... 560/218

[56] References Cited

U.S. PATENT DOCUMENTS

| | | | |
|---|---|---|---|
| 2,373,464 | 4/1945 | Dittmar | 560/215 |
| 2,704,770 | 3/1955 | Anspon | 560/218 |
| 3,228,973 | 1/1966 | O'Connor | 560/218 |
| 3,907,891 | 9/1975 | Guilbault et al. | 564/206 |

OTHER PUBLICATIONS

Zogorski, J. S. et al., *Chemical Engineering Progress*, May 1977, pp. 65–66.
Johnson, Delwin P. et al., *Analytical Chemistry*, vol. 33, (1961), pp. 910–913.
CA 88:7886u, (1978).
CA 88:51338r, (1978).

*Primary Examiner*—Paul J. Killos
*Attorney, Agent, or Firm*—Ernest G. Szoke; Henry E. Millson, Jr.; Neal T. Levin

[57] ABSTRACT

The monomer, trimethyl ammonium ethyl methacrylate methosulfate, is purified by passing same through a column of activated charcoal having a mean particle diameter of from about 0.5 mm to aboug 1.2 mm, the height to diameter ratio of the column being from about 3 to about 12 to 1. Monomer so treated can be polymerized to higher molecular weight polymers.

7 Claims, No Drawings

MONOMER PURIFICATION

BACKGROUND OF THE INVENTION

1. Field of the Invention

This invention relates to purification of trimethyl ammonium ethyl methacrylate methosulfate so that it is useful in preparation of high molecular weight polymers.

2. Description of the Prior Art

The monomer, trimethyl ammonium ethyl methacrylate methosulfate (TMAEMMS), generally available as an 80% aqueous solution, is homopolymerized or copolymerized with acrylamide thus forming cationic polymers useful as flocculants and retention aids in production of paper. Commercially available TMAEMMS typically contains about 800 to 1000 ppm of p-methoxy phenol (MEHQ), an inhibitor introduced to inhibit polymerization. Commercially available TMAEMMS also contains impurities such as methacrylic acid, methylmethacrylate, methanol, methyl chloride, amino alcohols and esters and other unknowns that retard, inhibit or act as chain regulators during polymerization. The result is often a low molecular weight polymer that is ineffective for its intended application. This is true despite effective removal of the inhibitor.

Attempts to treat the monomer by slurrying with activated carbon have not been found to be successful.

SUMMARY OF THE INVENTION

A process has been developed for purification of TMAEMMS by passing the monomer through an activated carbon column. The purified monomer, when polymerized yields high molecular weight polymers. This was most unexpected for several reasons. According to this process, useful monomer can be obtained despite presence of inhibitor in quantities as high as about 400 ppm. Further, it was discovered that mere removal of inhibitor to levels below about 400 ppm by means other than this process would not allow for polymerization of the monomer to the desired degree. Thus, it is believed that the present process in some way removes not only substantial quantities of inhibitor, but also removes other substances of known and unknown composition responsible for adversely affecting molecular weight of the polymer.

DESCRIPTION OF THE PREFERRED EMBODIMENTS

The monomer, TMAEMMS, as an aqueous solution, generally containing from about 80% by weight to about 30% by weight of monomer, preferably about 50% by weight monomer, is passed through a column packed with non-acid washed activated carbon, the particles of which have a mean particle diameter of from about 0.5 mm to about 1.2 mm. The height to diameter ratio of the column is from about 3 to about 12 to 1, preferably 8 to about 12 to 1. It is preferred that the activated carbon be pre-cooled to e.g., about 9 deg. C. to about 15 deg. C. This can be accomplished by passing cooled water through the column. It is also preferred that the monomer be pre-cooled to about 2 deg. C. to about 15 deg. C. prior to purification. Preferably, the monomer solution is saturated with air prior to passage through the column. Average retention time (ART) for the monomer in the column is from about five to about fifty minutes. However, for large production columns, average retention time is from about 10 to about 20 minutes, preferably about 15 minutes. This is shown by Example 14 (Table II) where an ART of 32 minutes resulted in polymerization in a large production column. Although not critical, the carbon efficiency ratio (ratio of monomer weight/activated carbon weight) is from about 16/1 to about 60/1.

Examples of useful activated carbons are:

NUCHAR WV-M: 20×50 mesh, bituminous coal, surface area=1100 sq. meters/gram, particle density=1.3–1.4 grams/cubic cm, voids in packed bed=45–55%, mean particle diameter=0.55–0.65 mm.

NUCHAR WV-G: 12×40 mesh, bituminous coal, surface area=1100 sq. meters/gram particle density=1.3–1.4 grams/cubic cm, voids in packed bed=45–55%, mean particle diameter=0.90–1.20 mm.

both manufactured by Westvaco. Mesh sizes set forth above and elsewhere herein are U.S. Sieve Series.

Evaluation of the Process

The following procedures were utilized in the Examples herein to evaluate the process.

COLUMN 1

A. Design

The dimensions and design of glass column 1 were as follows: Height=11 cm, diameter=3.5 cm, height/diameter ratio=3.1, head space=3.5 cm. The top of the column was open to the atmosphere for manual monomer addition. The bottom of the column contained glass wool just before the exit stopcock.

B. Process 50.0 grams of activated carbon were slurried with pure water. The slurry was added to the glass column. Care was taken when charging the slurry to avoid air entrapment. Several liters of pure water were passed through the column to pack the carbon. Concentrated monomer (80% by weight aqueous solution) was added to the column head space while at the same time the stopcock was fully opened. After the first 100 ml were passed through the column, the flow rate (ml/min.) was regulated to give the desired average retention time. Average retention time (ART) is defined as the length of time required for the monomer to pass through the packed column and is calculated by dividing volume of monomer in the packed column by the flow rate. Monomer collection started after a total of 150 ml were passed through the column. When the desired quantity of monomer was purified, the column was flushed with copious amounts of pure water until the wash water was free of monomer. The column was stored with pure water ready for re-use.

COLUMN 2

A. Design

The dimensions and design of stainless steel column 2 were as follows: Height=27.4 cm, width=2.5 cm, height/diameter ratio=11, head space=7.2 cm. The top of the column was open to the atmosphere for manual monomer addition. At the bottom of the column, two 100 mesh screens were sandwiched between a coarse screen just before the exit nipple. Tygon tubing was attached to the nipple leading to a stopcock and ultimately to a monomer collection reservoir. All stainless steel equipment was conditioned by passing hot 10% nitric acid solution through the system several times followed by several pure water washes prior to packing the column with activated carbon.

B. Process 74.5 grams of activated carbon were slurried with pure water. The slurry was added to the conditioned column. Care was taken when charging the slurry to avoid air entrapment. Several liters of pure water were passed through the column to pack the carbon. Concentrated monomer (80% by weight aqueous solution) was added to the column head space while at the same time the stopcock was fully opened. After the first 100 ml were passed through the column, the flow rate in ml/min. was regulated to give the desired ART. Monomer collection started after a total of 150 ml were passed through the column. When the desired quantity of monomer was purified, the column was flushed with copious amounts of pure water until the wash water was free of monomer. The column was stored with pure water ready for re-use.

COLUMNS 3 THROUGH 6

A. Design

The design for stainless steel columns 3 through 6 were as follows.

A stainless steel flexible hose connected the monomer reservoir tank to the top of the column. The monomer tank was equipped with an air inlet sparge tube and refrigerated cooling coils. Stainless steel piping was connected from the bottom of the column to a 3 micron cartridge filter leading to a monomer collection reservoir. All stainless steel equipment was conditioned by passing hot one percent nitric acid solution through the system several times followed by several pure water washes prior to packing the column with activated carbon. Note that columns 5 and 6 are large production columns.

Dimensions of Column 3

Height=26.7 cm, diameter=21.6 cm, height/diameter ratio=1.24, head space=39.4 cm.

Dimensions of Column 4

Height=48.3 cm, diameter=21.6 cm, height/diameter ratio=2.24, head space=17.8 cm.

Dimensions of Column 5

Height=76.2 cm, diameter=7.8 cm, height/diameter ratio=9.8, head space=15.2 cm.

Dimensions of Column 6

Height=128.0 cm, diameter=12.8 cm, height/diameter ratio=10.0 head space=1.6 cm.

B. Process

Activated carbon particles were slurried with equal parts of pure water in a suitable container. The slurry was charged to the conditioned column and then backwashed three times with pure water. The carbon in the column was allowed to settle for several hours. The carbon was pre-cooled to 9-15 deg. C. by passing 200 pounds of 2-15 deg. C. water through the column. The monomer was diluted with pure water to 50% by weight active material, charged to the monomer tank, pre-cooled to 2-15 deg. C. and sparged with dry air to approximately 5-12 psi. The monomer was pressure fed through the column at the desired ART and collected.

All purified and non-purified TMAEMMS monomers were analyzed for p-methoxy phenol (MEHQ) polymerization inhibitor by a simple colorimetric determination (Reference: Analytical Chemistry, Vol. 33, No. 7, June 1961, pages 910-913).

The activated carbons used are set forth below including those outside of the scope of the invention.

NUCHAR WV-M (Westvaco): 20×50 mesh, bituminous coal, surface area=1100 sq. meters/gram, particle density=1.3-1.4 grams/cubic cm, voids in packed bed=45-55%, mean particle diameter=0.55-0.65 mm.

NUCHAR WV-L (Westvaco): 8×30 mesh, bituminous coal, surface area approximately 1100 sq. meters/gram, particle density=1.35-1.45 grams/cubic cm, voids in packed bed=45-55%, mean particle diameter=1.4-1.7 mm.

NUCHAR WV-G (Westvaco): 12×40 mesh, bituminous coal, surface area=1100 sq. meters/gram, particle density=1.3-1.4 grams cubic cm, voids in packed bed=45-55%, mean particle diameter=0.90-1.20 mm.

NUCHAR HW-40 (Westvaco): 12×40 mesh, acid washed bituminous coal, surface area=1050-1200 sq. meters/gram, particle density=1.3-1.4 grams/cubic cm, voids in packed bed=45-55%, mean particle diameter=0.9-1.2 mm.

FILTASORB-300 (Calgon): 8×30 mesh, bituminous coal, surface area=1100 sq. meters/gram, voids in packed bed=40%.

Determination of Apparent Molecular Weight of Polymers

The apparent molecular weight of the polymers prepared from the monomer samples which have been purified in an indication of the efficacy of the monomer purification process. That is, the higher the molecular weight of the polymer, the purer the monomer from which the polymer was prepared.

The apparent molecular weight of the polymers were determined through a 0.1% by weight actives viscosity measurement in the presence of 1N NaCl. To 200 grams pure water was added 1 gram (1.000 gram accuracy) of copolymer emulsion while mixing. Pure water was added to the solution to adjust the concentration to 0.1% by weight polymer actives. The solution was allowed to mix for 2 hours at 25 deg. C. After the mixing period elapsed, NaCl was added to the solution at a ratio of 5.85 grams NaCl per 100 grams of solution. Ample time was allowed for the salt to dissolve in the solution. The viscosity of the solution was determined by using Brookfield Engineering Labs. UL adapter attachment on a Brookfield Viscometer. The higher the viscosity reading, the higher the molecular weight of the copolymer. A minimum viscosity of 3.8 cps represents a molecular weight of five to seven million for the polymer. This range is most desirable for polymers used as flocculants and drainage aids in paper manufacture.

Polymerization of the Monomer

High molecular weight cationic copolymers were prepared from the various treated monomers and their viscosities determined as described above. In brief, polymerization was achieved by using conventional emulsion polymerization techniques, namely, (1) dissolving 248.3 grams acrylamide and 99.6 grams TMAEMMS (52.3% active) monomers in 297.9 grams water to form an aqueous phase, (2) dissolving 31.5 grams Sorbitan monooleate in 247.7 grams kerosene to form an oil phase, (3) emulsifying the aqueous phase containing acrylamide and TMAEMMS in the oil phase to prepare a water-in-oil monomer emulsion, (4) polymerizing the monomers dissolved in the aqueous phase of the water-in-oil emulsion using a free radical yielding initiator as catalyst to obtain the copolymer and (5) adding 38.4 grams of a water soluble surfactant (HLB approx. 9) to the water-in-oil emulsion in order to render water solubility to the emulsion.

For a fuller understanding of the nature and advantages of this invention, reference may be made to the following examples. These examples are given merely to illustrate the invention and are not to be construed in a limiting sense.

CONTROL

Attempts were made to copolymerize acrylamide with "as received" TMAEMMS from two different monomer suppliers in a water-in-oil emulsion. The MEHQ inhibitor levels of both TMAEMMS monomer samples were in the range of 800 to 1000 ppm. The results indicated incomplete polymerizations in both instances. Incomplete polymerization is evidenced by a high level of unreacted monomer. This is determined by titration for presence of acrylamide and by the fact that the measured heat of polymerization is only about 20% of normal.

COMPARATIVE EXAMPLES A–E 50.0 grams of Nuchar WV-L (Example A) and Nuchar HW-40 (Example B), were used to purify 100 mls TMAEMMS in column 1. 50.0 grams of Filtasorb-300 (Examples C-E) were used to purify 300 mls TMAEMMS in column 1.

EXAMPLES 1–4

The comparative examples were repeated with 50.0 grams of Nuchar WV-M purifying 600 ml TMAEMMS in column 1 (Examples 1-3) and 50 grams of Nuchar WV-G purifying 150 ml TMAEMMS in column 1 (Example 4).

EXAMPLES 5–7

74.5 grams of Nuchar WV-G were charged to column 2 and 400 mls TMAEMMS were purified. The carbon efficiency ratio was 16/1.

EXAMPLE 8

10 pounds of Nuchar WV-M were charged to column 3 to purify 120 pounds TMAEMMS (Example 8).

EXAMPLE 9

16.2 pounds of Nuchar WV-G were charged to column 4 to purify 400 pounds TMAEMMS. The monomer in this column prematurely polymerized during the purification step and was not screened in a water-in-oil emulsion polymerization.

EXAMPLES 10–12

5 pounds of Nuchar WV-G were charged to a column 5 and 240 pounds of 50% by weight active TMAEMMS were purified. The carbon efficiency ratio of column 4 was 60/1.

EXAMPLE 13

17.5 pounds of Nuchar WV-G were charged to column 6 and 300 pounds of 50% by weight active TMAEMMS were purified.

EXAMPLE 14

17.5 pounds of Nuchar WV-G were charged to column 6 and 300 pounds of 50% by weight active TMAEMMS were passed through the column. During purification, the monomer prematurely polymerized and therefore was not screened in a water-in-oil emulsion polymerization.

EXAMPLE 15

165 grams of 78% by weight active TMAEMMS and 3.3 grams Nuchar WV-G were charged to a 500 ml round bottom flask. This was 2.6% by weight of activated carbon based on weight of actual monomer present. The contents of the flask were mixed for several hours open to air at 25 deg. C. Aliquots were drawn periodically and the MEHQ level was determined. Table I sets forth the data obtained.

TABLE I

| Aliquot No. | Mixing Time (hrs.) | MEHO (ppm) |
|---|---|---|
| Start | 0 | 764 |
| 1 | 1 | 681 |
| 2 | 2 | 589 |
| 3 | 3 | 545 |
| 4 | 5 | 589 |

Table II below sets forth the data obtained in comparative Examples A–E and Examples 1 through 15.

TABLE II

| Ex. No. | Activated Carbon Column | Col. Ht/Diam. Ratio | Activated Carbon | ART (min) | MEHQ Level (ppm) Start | MEHQ Level (ppm) End | Visc. of 0.1% Polymer (cps) |
|---|---|---|---|---|---|---|---|
| Control | — | — | — | — | 800+ | 800+ | X |
| A | 1 | 3.10 | WV-L | 45 | 800 | 277 | X |
| B | 1 | 3.10 | HW-40 | 49 | 800 | 76 | X |
| C | 1 | 3.10 | F-300 | 45 | 800 | 300 | 3.65 |
| D | 1 | 3.10 | F-300 | 45 | 800 | 300 | 3.61 |
| E | 1 | 3.10 | F-300 | 45 | 800 | 300 | 3.40 |
| 1 | 1 | 3.10 | WV-M | 45 | 825 | 27 | 4.62 |
| 2 | 1 | 3.10 | WV-M | 45 | 825 | 221 | 3.92 |
| 3 | 1 | 3.10 | WV-M | 45 | 825 | 365 | 4.23 |
| 4 | 1 | 3.10 | WV-G | 40 | 825 | 0 | 3.95 |
| 5 | 2 | 11.00 | WV-G | 25 | 825 | 4 | 3.91 |
| 6 | 2 | 11.00 | WV-G | 20 | 825 | 179 | 4.16 |
| 7 | 2 | 11.00 | WV-G | 13 | 825 | 214 | 3.94 |
| 8 | 3 | 1.24 | WV-M | 18 | 810 | 323 | X |
| 9 | 4 | 2.24 | WV-G | 20 | 812 | — | * |

TABLE II-continued

| Ex. No. | Activated Carbon Column | Col. Ht/Diam. Ratio | Activated Carbon | ART (min) | MEHQ Level (ppm) Start | MEHQ Level (ppm) End | Visc. of 0.1% Polymer (cps) |
|---|---|---|---|---|---|---|---|
| 10 | 5 | 9.80 | WV-G | 15 | 800 | 0 | 3.90 |
| 11 | 5 | 9.80 | WV-G | 10 | 800 | 0 | 3.98 |
| 12 | 5 | 9.80 | WV-G | 5 | 800 | 44 | 3.90 |
| 13 | 6 | 10.00 | WV-G | 14 | 800 | 8 | 3.83 |
| 14 | 6 | 10.00 | WV-G | 32 | 800 | — | * |
| 15 | — | — | WV-G | — | 764 | 589** | — |

X = Incomplete polymerization.
*Monomer polymerized in column.
**After slurrying for 5 hours.

As shown by the above data, mere removal of inhibitor to less than about 400 ppm, but not using this process, will not allow for polymerization of the monomer to the desired degree, viz., a minimum viscosity of 3.8 cps. See comparative Example B where despite removal of most of the inhibitor, i.e., only 76 ppm inhibitor remains, polymerization was incomplete. On the other hand, see also Examples 1, 3 and 4 which were carried out according to this invention where the inhibitor level varied from 0 to 365 ppm and the viscosities were found to be favorable, i.e., between 3.95 and 4.62.

Further, it would be expected that the longer the residence time in the column, the greater is the removal of impurities. However, See Table II, Example 14 which describes use of a large production column. Here, too long a residence time in the column will result in monomer polymerization.

While the invention has been described with reference to certain specific embodiments thereof, it is understood that it is not to be so limited since alterations and changes may be made therein which are within the full intended scope of the appended claims.

What is claimed is:

1. A process of purifying the monomer, trimethyl ammonium ethyl methacrylate methosulfate, by removing polymerization inhibiting impurities therefrom which comprises passing said monomer through a column packed with non-acid washed activated carbon having a mean particle diameter of from about 0.5 mm to about 1.2 mm, the height to diameter ratio of the column being from about 3 to about 12 to 1 and the average retention time of said monomer in said column being from about five to about fifty minutes, said process carried out under air sparge.

2. The process of claim 1 wherein said monomer is in the form of an aqueous solution containing from about 80 to about 30 percent by weight of monomer.

3. The process of claim 2 wherein said average retention time is from about ten to about 20 minutes.

4. The process of claim 3 wherein said height to diameter ratio of said column is from about 8 to about 12 to 1.

5. The process of claim 4 wherein said activated carbon is pre-cooled.

6. The process of claim 5 wherein said monomer is pre-cooled.

7. The process of claim 6 wherein said average retention time is about fifteen minutes.

* * * * *